(12) United States Patent
Kellogg et al.

(10) Patent No.: US 7,767,874 B2
(45) Date of Patent: Aug. 3, 2010

(54) MEDICAL DEVICE AND PROCESS

(75) Inventors: Donald L. Kellogg, Aptos, CA (US); Jack Kellogg, Aptos, CA (US)

(73) Assignee: Telesto Holding, LLC, Arlington Heights, IL (US)

( * ) Notice: Subject to any disclaimer, the term of this patent is extended or adjusted under 35 U.S.C. 154(b) by 301 days.

(21) Appl. No.: 11/605,098

(22) Filed: Nov. 28, 2006

(65) Prior Publication Data
US 2008/0125688 A1    May 29, 2008

(51) Int. Cl.
A61F 15/00    (2006.01)
B32B 3/26    (2006.01)
B32B 5/18    (2006.01)

(52) U.S. Cl. .................. 602/48; 428/304.4; 442/30

(58) Field of Classification Search .................. 602/41, 602/42, 43, 56; 428/304.4, 319.3, 319.7, 428/158, 181, 212; 442/30, 56
See application file for complete search history.

(56) References Cited

U.S. PATENT DOCUMENTS

| | | |
|---|---|---|
| 2,533,504 A | 12/1950 | Poor |
| 2,699,165 A | 1/1955 | Ferrier |
| 2,781,041 A | 2/1957 | Weinberg |
| 2,943,859 A | 7/1960 | Koski et al. |
| 3,173,420 A | 3/1965 | Mazzoni et al. |
| 3,403,676 A | 10/1968 | Gibbons |
| 3,454,010 A | 7/1969 | Lilligren |
| 3,459,179 A | 8/1969 | Olesen |
| 3,548,819 A | 12/1970 | Davis et al. |
| 3,561,435 A | 2/1971 | Nicholson |
| 3,728,875 A | 4/1973 | Hartigan |
| 3,745,998 A | 7/1973 | Rose |
| 3,845,769 A | 11/1974 | Shaw |
| 3,862,629 A | 1/1975 | Rotta |
| 3,885,554 A | 5/1975 | Rockwell |
| 3,901,225 A | 8/1975 | Sconce |
| 3,942,518 A | 3/1976 | Tenteris et al. |
| 3,975,929 A | 8/1976 | Fregeolle |
| 4,013,069 A | 3/1977 | Hasty |
| 4,030,488 A | 6/1977 | Hasty |

(Continued)

OTHER PUBLICATIONS

Foam-tech comparison of open cell foam and closed cell foam.*

*Primary Examiner*—Patricia M Bianco
*Assistant Examiner*—Tarla R Patel
(74) *Attorney, Agent, or Firm*—Husch Blackwell Sanders LLP Welsh & Katz

(57) ABSTRACT

A patient-friendly medical device is provided for removal of excess fluids from body tissue and is particularly useful to treat soft tissue inflammation, damage, edema and/or lymphedema. The comfortable medical device comprises a composite multilayered assembly that provides a gradient pressure compression device to compress body tissue of a patient in a controlled and graduated manner. The composite multilayered assembly can have an inner and/or outer layer to enhance uniform distribution of compression about the affected portion of the patient and can have flexible intermediate layers with elastomeric components such as foamed chips, foamed pieces, and/or chopped foam that can have a different density and/or size and/or shape to form channels (canals) therebetween to enhance flow of excess fluids from the body tissue of the patient. The channels or canals can create zones of gradient pressure to help move excess fluid from the tissue of the affected portion of the body of the patient.

18 Claims, 7 Drawing Sheets

U.S. PATENT DOCUMENTS

| | | |
|---|---|---|
| 4,180,065 A | 12/1979 | Bowen |
| 4,320,746 A | 3/1982 | Arkans et al. |
| 4,370,975 A | 2/1983 | Wright |
| 4,374,518 A | 2/1983 | Villanueva |
| 4,402,312 A | 9/1983 | Villari et al. |
| D275,219 S | 8/1984 | Scales, Jr. |
| 4,552,133 A | 11/1985 | Kawaguchi |
| 4,583,522 A | 4/1986 | Aronne |
| 4,743,499 A * | 5/1988 | Volke ................ 428/317.3 |
| 4,773,397 A | 9/1988 | Wright et al. |
| 4,862,879 A | 9/1989 | Coombs |
| 4,922,893 A | 5/1990 | Wright et al. |
| 4,938,208 A | 7/1990 | Dye |
| 4,961,418 A | 10/1990 | McLaurin-Smith |
| 5,025,781 A | 6/1991 | Ferrari |
| 5,063,910 A | 11/1991 | Cartier |
| 5,108,426 A | 4/1992 | Biro et al. |
| 5,109,832 A | 5/1992 | Proctor |
| 5,117,812 A | 6/1992 | McWhorter |
| 5,171,211 A | 12/1992 | Deasy, Jr. |
| 5,172,689 A | 12/1992 | Wright |
| 5,228,142 A | 7/1993 | Yoswein-McGreen |
| 5,233,974 A | 8/1993 | Senoue |
| 5,245,990 A | 9/1993 | Bertinin |
| 5,310,400 A | 5/1994 | Rogers |
| 5,404,591 A | 4/1995 | Brinnand |
| 5,415,624 A | 5/1995 | Williams |
| 5,437,621 A * | 8/1995 | Andrews et al. ............. 602/42 |
| D371,845 S | 7/1996 | Varn |
| 5,592,953 A * | 1/1997 | Delao ..................... 128/882 |
| 5,618,263 A | 4/1997 | Alivizatos |
| 5,718,669 A | 2/1998 | Marble |
| 5,728,055 A | 3/1998 | Sebastian |
| 5,766,141 A | 6/1998 | Gould |
| 5,769,804 A | 6/1998 | Harris et al. |
| 5,868,692 A | 2/1999 | Michniewicz |
| 5,925,007 A | 7/1999 | Ashline |
| 5,976,099 A | 11/1999 | Kellogg |
| 5,987,641 A | 11/1999 | Walker |
| 6,006,751 A | 12/1999 | Spitzer |
| D438,625 S | 3/2001 | Kellogg |
| 6,200,286 B1 | 3/2001 | Zamani |
| D454,639 S | 3/2002 | Kellogg |
| 6,485,594 B1 * | 11/2002 | Pabsch et al. ............. 156/213 |
| 2003/0050589 A1 * | 3/2003 | McDevitt et al. ............ 602/41 |

* cited by examiner

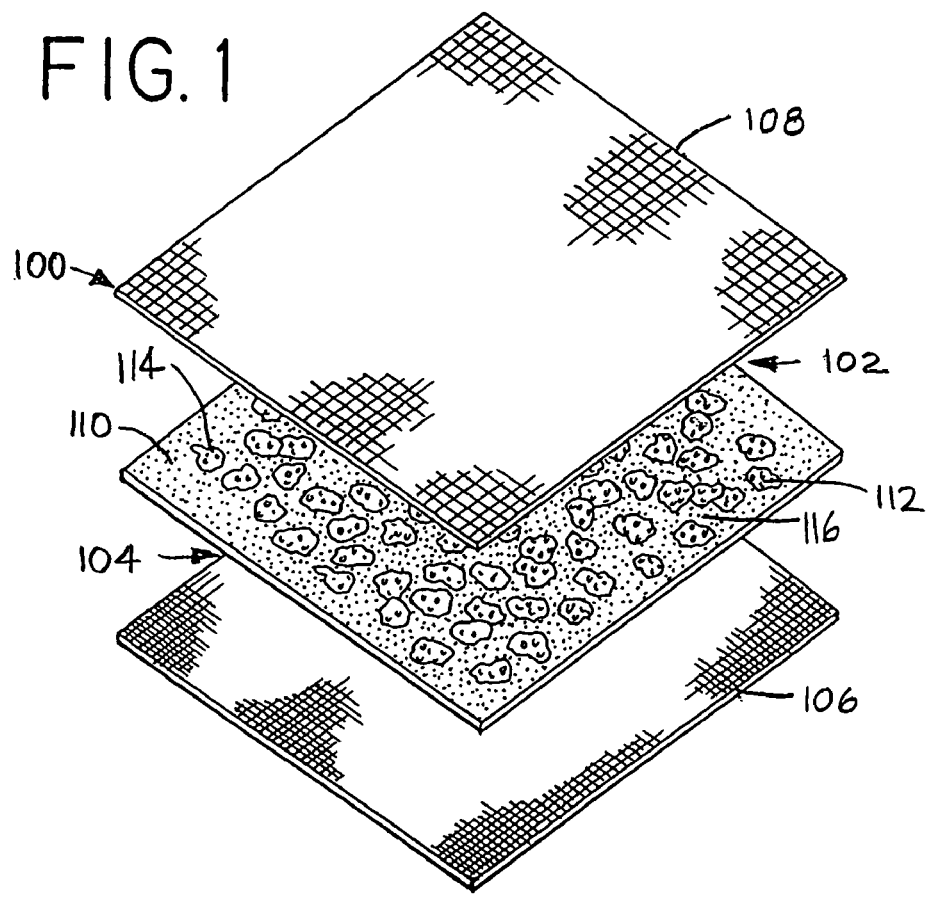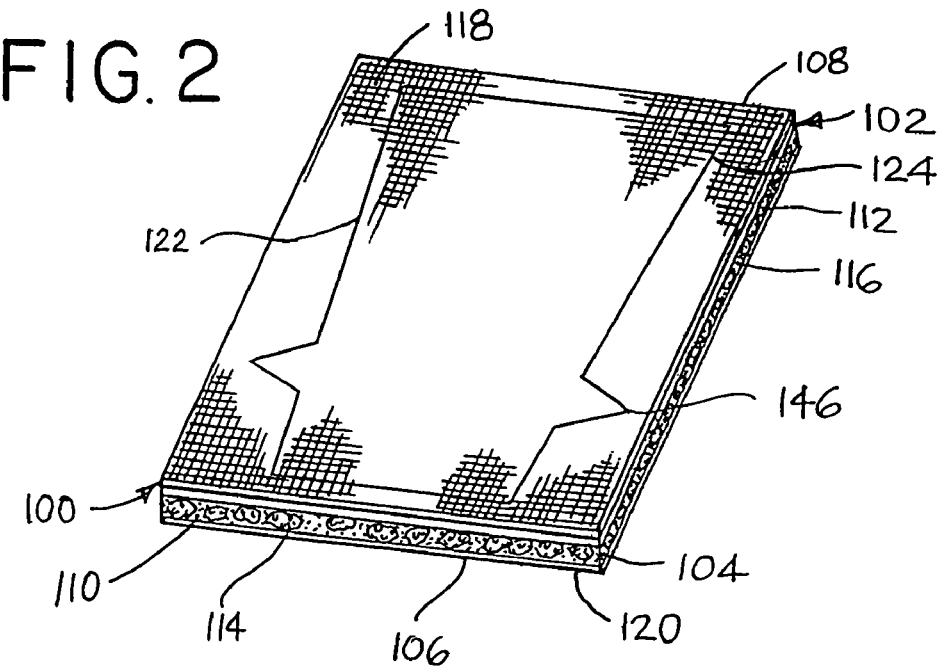

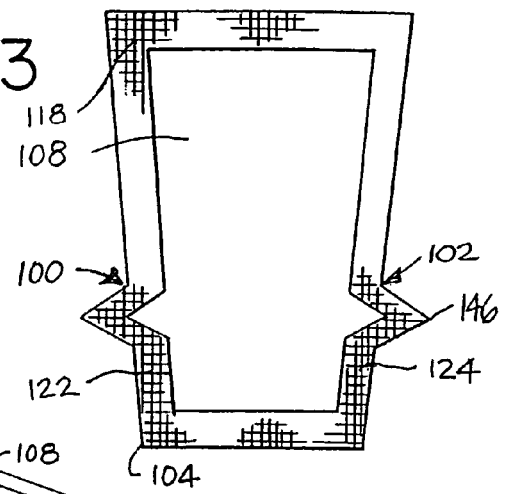
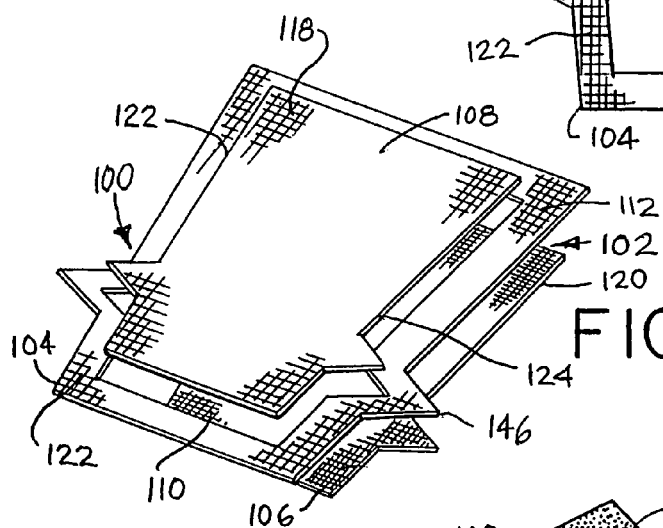
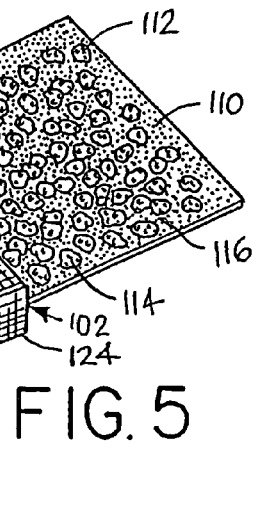

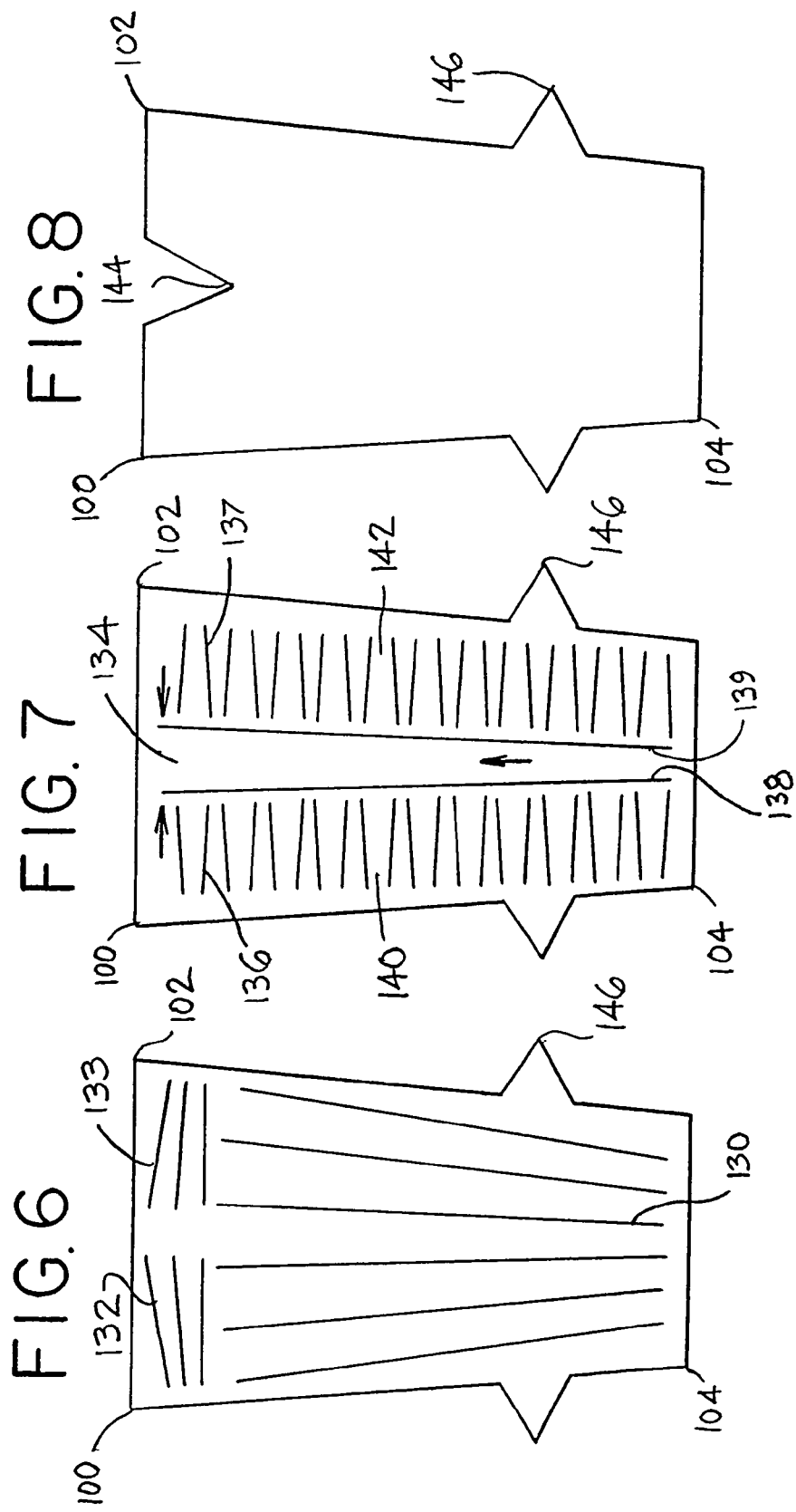

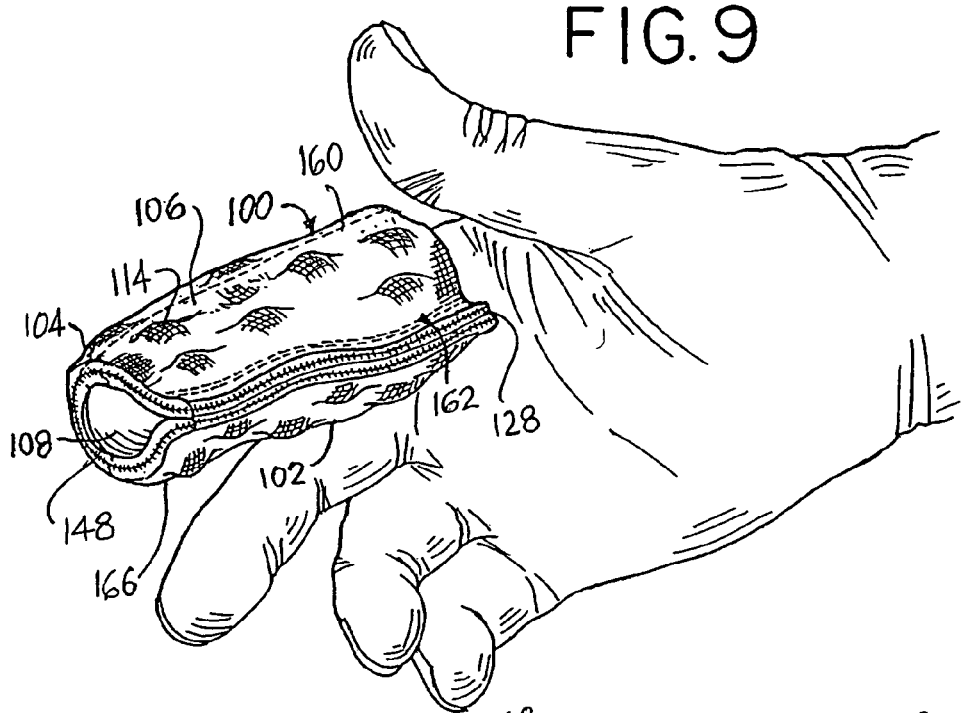
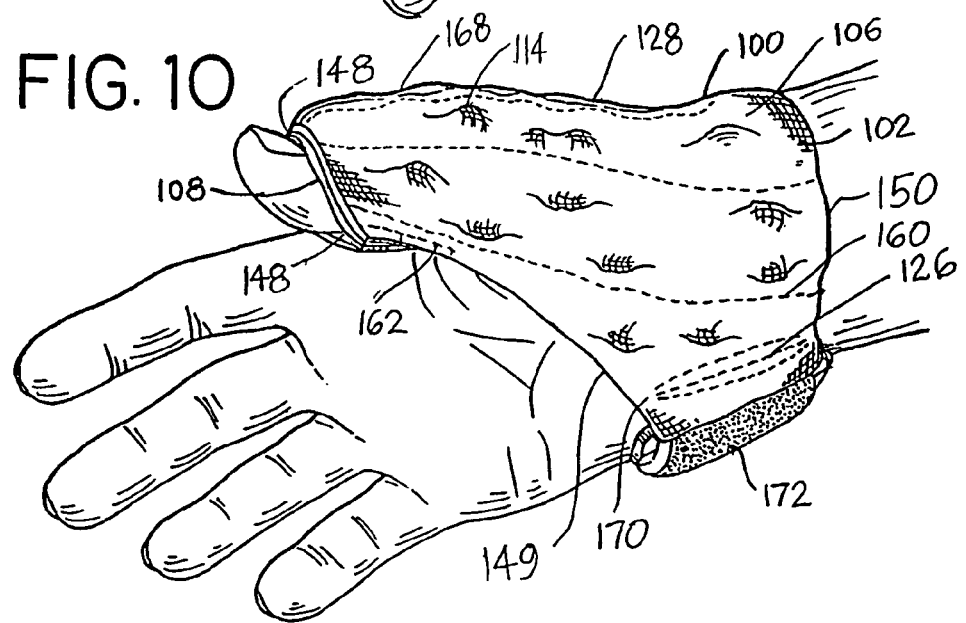

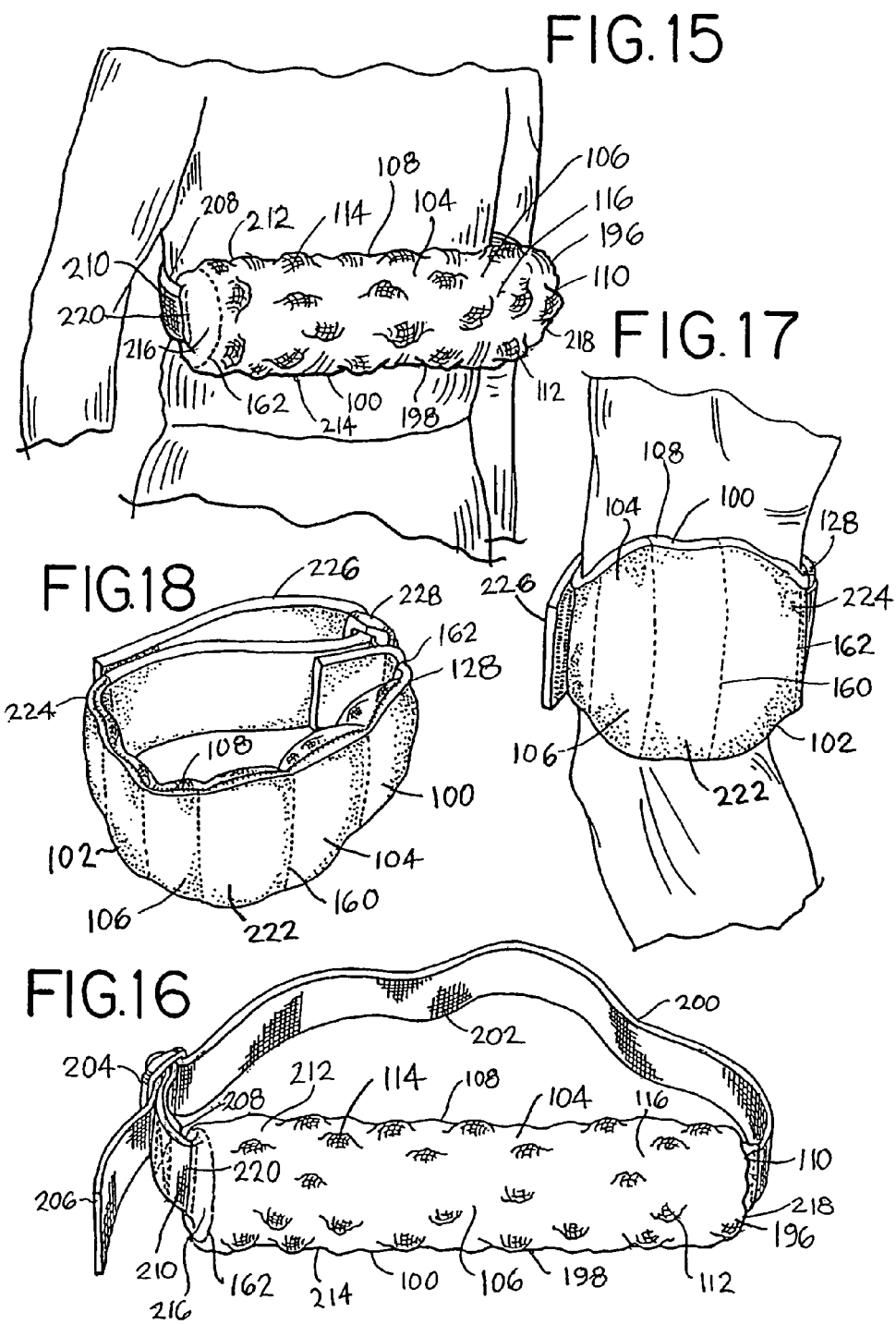

MEDICAL DEVICE AND PROCESS

BACKGROUND OF THE INVENTION

This invention relates to a medical device and process and more particularly, to a gradient pressure compression device for removal of excess fluids from body tissue and a method of constructing and using the gradient pressure compression device.

By way of background, the lymphatic system is organized like the blood system and has numerous tiny vessels connected to a network of larger vessels through which a liquid medium containing solutes and particulates is transferred. A healthy lymphatic system continuously drains lymphatic fluid comprising a mixture of lymph, water, proteins and other matter, away from various interstitial areas of the body and back into the blood system. Lymph is the liquid medium or solvent of the lymphatic system.

The lymph fluid is pumped through the lymphatic system and away from various body areas by both the action of adjacent muscle tissue and contraction of the larger lymphatic vessels. Foreign matter is filtered out of the lymph fluid as the fluid passes through bundles of lymph nodes during its passage through the lymphatic system. The lymph nodes also monitor the contents of the lymph fluid to determine if any appropriate immune reactions should be initiated by the host's immune system. The lymph is then transferred back into the blood system after this filtration.

Lymphedema is a deficiency, blocking or dysfunction of the lymphatic system that limits the flow of lymph fluid from a body area. The most frequent causes of lymphedema include primary insufficiency, traumatic accidents, chronic venous diseases, radiation therapy of the lymph nodes, prostate operations, mastectomies, amputations and other surgical operations. Lymphedema most typically occurs in arms and legs, but most other body areas can become lymphedemic, such as the head, genitals and the trunk of the body.

Lymphedema and edema can cause reduction in mobility, pain, embarrassment and serious emotional depression. Rapid swelling, such as caused by radiation therapy or a surgical operation, can be especially painful as the body tissue is effectively being torn apart by the fluid pressure. The World Health Organization has estimated that approximately 500 million people suffer from some form of lymphedema.

Individual cases of lymphedema are typically diagnosed as belonging to either a primary or a secondary class. Primary lymphedema is a condition where the lymphatic system is chronically or acutely overwhelmed by the volume of lymphatic fluid to be evacuated. Chronic primary lymphedema is often a genetically determined condition. Acute primary lymphedema, and edema, can be caused by an injury or trauma where the lymph system is properly functioning but is temporarily overwhelmed. Swelling and/or edema caused by minor burns, sprains and other injuries are typically alleviated after a few days or weeks in a patient in generally good health. However, even temporary swelling can be painful to the patient and can result in fibrosis (the presence of tough, scarlike tissue).

Secondary lymphedema is typically presents as a relatively sudden cessation or deep reduction of the functionality of a portion of the lymphatic system. The most frequently occurring causes of secondary lymphedema include radiation therapy, mastectomies, amputations and other surgical operations.

Regardless of cause or class, a significant limitation or attenuation of the necessary progress of lymphatic fluid through the lymphatic system may result in a concentration or swelling of the protein bearing lymph fluid in the interstitial area of the soft tissue of an affected limb or body region. Chronic lymphedema more often results in severe and even life threatening consequences than acute edemas.

Any sustained accumulation of proteins delivered to the body tissue by the blood capillaries, and not removed by the lymphatic system, will cause a swelling of fluid in the interstitial areas of the body tissues. The oxygenation of adjacent tissue is then reduced and the healing process is retarded. A localized accumulation of proteins further aggravates this situation by directly stimulating chronic inflammation. Chronic inflammation usually results in the formation and dilation of additional capillaries. These additional blood vessels deliver undesirable excess heat to the swollen area. This undesirable heating of the protein rich interstitial fluid increases the incidence and virulence of opportunistic bacteriological infections.

Conventional treatment techniques for lymphedema include the use of benzo-pyrene drugs, massage therapy, physical exercise, compression bandages and compression garments. Treatment strategies that apply physical pressure to a swollen, edemic or lymphedemic body area can be divided into those which provide intermittent forced compression and those which maintain a relatively constant pressure over time. Looking first at intermittent forced compression devices, Ferrari U.S. Pat. No. 5,025,781 discloses an inflatable cuff that is alternately inflated and deflated to deliver a uniform blanket compression against the circumference of a swollen limb. This action may, however, exacerbate the patient's condition by collapsing blood vessels, increasing leakage into the interstitial areas and obstructing lymphatic outflow.

Bertinin U.S. Pat. No. 5,245,990 describes an inflatable sheath which has tubes that are inflated and deflated in a sequence starting from the most distal and ending at the most proximal. Apparently, Bertinin intends to supply a wave-like massage to the swollen limb. Bertinin's method of timed and sequential inflation and deflation is similar to the invention of Ferrari in that a uniform blanket pressure is exerted against the swollen tissue at any particular moment. This blanket pressure can be ineffective. Furthermore, compressive devices which include pneumatic pumps can cause damage to the health of the patient and must typically by applied by a trained medical practitioner.

Schneider packs can be used to apply constant pressure to a body part. Schneider packs consist of small packs of randomly placed pieces of high density foam bound within a tubular cloth pouch or tube. Schneider packs are incorporated into bandaging and usually cannot be attached by the patient without assistance.

A Reid Sleeve device for treating lymphedema was made by Tony Reid, M.D. and Donald L. Kellogg, one of the applicants of this patent application. The Reid Sleeve device comprises a sheet of convoluted plastic foam and means to push the extending elements or fingers of the convoluted foam sheet against a swollen body part of a patient. The foam fingers are prearranged neatly on the foam sheet in rows and columns and create a grid pattern of high and low pressure areas when pressed against the patient's body area. The convoluted foam sheet is encased in an inner lining of a SPANDEX™ material and an outer lining of relatively heavy nylon fabric. Adjustable VELCRO™-type straps and matching D-ring straps are sewn into the outer lining. The convoluted plastic foam sheet of the Reid Sleeve device is secured and pressed against and/or around a body part of the patient. A medical practitioner can use a pressure gauge while applying the Reid Sleeve device to cinch the VELCRO™-type straps to a particular pressure point or to within a preferred pressure range. The Reid Sleeve device, however, can have disadvantages. The Reid Sleeve arm design is heavy and can weighs over three pounds. Furthermore, the Reid Sleeve device is not configurable to apply pressure to a combination of a limb and an adjacent body area (e.g. leg and groin, leg and hip, arm and shoulder, and etc.) with a single assembly device. The use of the heavy nylon fabric in the Reid Sleeve device, as well as the construction of the Reid Sleeve device, can also limit the adjustability of the Reid Sleeve device to comfortably and appropriately fit different body sizes.

It is, therefore, desirable to provide an improved medical device and process to provide for enhanced medical treatment of lymphedema, edema and other soft tissue swelling.

BRIEF SUMMARY OF THE INVENTION

An improved medical device is provided for removal of excess fluids from body tissue. Advantageously, the improved medical device is easy to use, portable, light weight, easily transportable, comfortable, and economical. Desirably, the improved medical device is particularly useful to treat soft tissue inflammation, damage, edema and/or lymphedema in an effective and efficient manner. The improved medical device produced unexpected surprisingly good results.

The improved medical device comprises a composite multilayered assembly for compressing body tissue of a patient in a controlled and graduated manner. In one preferred form, the composite multilayered assembly has an outer layer and an inner layer which cooperate with each other to enhance uniform distribution of compression about the affected portion of the patient. The inner layer is positioned to engage or contact the skin about an affected portion of the body of a patient. The inner and outer layers can comprise elastic fabric layers with a polyester-type fabric and a LYCRAT™-type stretchable fabric comprising SPANDEX™ or elastane fabric with polyurethane and/or polyethylene glycol. Preferably, the inner layer has a lower denier with thinner threads and more stretch than the outer fabric to more comfortably contact or cushion the skin about the affected portion of the patient.

The composite multilayered assembly also comprises flexible intermediate layers that are positioned between the outer and inner layers. The flexible intermediate layers can comprise an elastomeric layer and a resilient layer having a different composition and structure than the inner and outer layers. The elastomeric layer can be made of foam rubber and is preferably flexible to conform to the affected portion of the body of the patient. The resilient layer can comprise an array, series, set, matrix, pattern, and plurality of elastomeric components, such as foamed chips, foamed pieces, foamed parts, foamed sections, cut foam, and/or chopped foam, that are secured to the elastomeric layer. Preferably, at least some of the elastomeric components (e.g. chopped foam) have a different density and/or size and/or shape than the other elastomeric components in the medical device. In the preferred form, the elastomeric components (e.g. chopped foam) are spaced apart from each other to form channels or canals therebetween to enhance flow of excess fluids from the body tissue of the patient. Each of the elastomeric components (e.g. chopped foam) can have a maximum span and size that is smaller than the elastomeric layer, outer layer, and inner layer.

The improved medical device preferably comprises a gradient pressure compression device wherein the elastomeric components (e.g. chopped foam) cooperates with each other and the channels or canals to create zones of gradient pressure to help move excess fluid from the tissue of the affected portion of the body of the patient. The inner layer can facilitate penetration of the elastomeric components (e.g. chopped foam) against or into the soft issue of the affected portion of the body of the patient.

The composite multilayered assembly of the medical device can have sewn or sealed edges and a compressed portion about an opening (e.g. hole), V-shaped notch, V-shaped extension and/or protuberance for accommodating and receiving the affected portion of the body of the patient, such as a joint, shoulder, knee, elbow, ankle, foot, at least one toe, at least one finger, a hand, wrist, upper arm, lower arm, thigh, chest, stomach, back, upper leg, lower leg, groin, genitals, neck, face, and head.

The improved medical device can also have a casing with casing walls providing a case or periphery which is positioned peripherally about at least a portion of the flexible intermediate layers to help facilitate even distribution of variegated pressure from the elastomeric components (e.g. chopped foam) and the channels or canals about the affected portion of the body of the patient.

The improved medical device can further have one or more converging sections with curved or substantially straight tapered lines or tapered channels or canals for augmenting gradient pressure and enhancing flow of excess fluid away from the affected portion of the body of the patient. The tapered lines can include longitudinally extending tapered lines and/or laterally extending tapered lines. The tapered channels or canals including at least one longitudinally extending tapered channel or canal and/or at least one laterally extending tapered channel or canal.

The improved medical device can have an outer and/or inner layer with pleats, seams, one or more zippers, buttons or other fasteners, and/or can have stitches of varying lengths to provide different amounts of stretch to different portions (sections) of the medical device. The stitches can include longer stitches for allowing the inner and outer layers to more comfortably conform to the body of the patient as the patient moves to help maintain constant compression and facilitate removal of excess fluid from the affected portion of the body of the patient. The stitches can also include shorter stitches for less stretch and a tighter fit of the medical device about the affected portion of the patient for helping prevent slippage of the medical device during wear of the medical device by the patient and for facilitating channeling and removal of excess fluid away from the affected portion of the patient.

The medical device can comprise a hand-shaped or foot-shaped medical device with elastic bands sewn or secured between digits of the medical device about the fingers or toes of the patient to enhance pressure from the elastomeric components (e.g. chopped foam) to further assist in removing excess fluid away from the affected portion of the patient.

A splinted assembly can also be constructed using the medical device. In the splinted assembly, a splint is secured to the medical device and a fabric overlay is sewn or otherwise secured to the medical device over the splint. The fabric overlay cooperates with the medical device to provide a pocket for receiving the splint. The pocket and the medical device cooperate with each other to allow lateral movement of the splint so as to accommodate movement of a patient's fingers, toes or other body portion that extends from the splint, as well as reduce stiffness of the affected portion of the body and enhance removal of excess fluid form the affected portion of the body of the patient.

In another preferred form, a cylindrical type or style medical device comprises a composite multilayered cylindrical type or style assembly for removal of excess fluids from body tissue of a patient and/or for treatment of large lymphoceles or lymphocytes and conditions where excess body fluid can cause skin folding or softening of fibrous tissue. The composite multilayered cylindrical type or style assembly can have flexible layers including an elastomeric layer comprising a central core and a resilient layer secured to the elastomeric layer. Elongated strapping comprising at least one strap can secure the medical device to or about an affected portion (area) of the body of the patient.

The elastomeric layer in the cylindrical type or style medical device can be made of foam rubber and is preferably flexible to conform to the affected portion of the body of the patient. The resilient layer in the cylindrical medical device can comprise an array, series, set, matrix, pattern, and plurality of elastomeric components, such as foamed chips, foamed pieces, foamed parts, foamed sections, cut foam, and/or chopped foam; that are secured to the elastomeric layer. Some of the elastomeric components (e.g. chopped foam) in the cylindrical medical device can have a different density and/or size and/or shape than the other elastomeric components in the cylindrical medical device. Desirably, the elastomeric components (e.g. chopped foam) in the cylindrical medical device are spaced apart from each other to form channels or canals therebetween to enhance flow of excess fluids from the body tissue of the patient. Each of the elastomeric components (e.g. chopped foam) in the cylindrical medical device can have a maximum span and size that is smaller than the elastomeric layer, outer layer, and inner layer. Significantly, the elastomeric components (e.g. chopped foam) of the cylindrical medical device cooperate with each other to provide micro-zones of high and low pressure to facilitate movement of excess fluid away from the affected area or skin folds of the body of the patient.

The composite multilayered cylindrical assembly of the cylindrical type or style medical device can have an outer cover that can comprise a shell. Preferably, the outer cover has a different composition and structure than the elastomeric layer and the resilient layer and is larger than the elastomeric components (e.g. chopped foam). The outer cover can have an outer protective sleeve with axially opposite end sections. The outer protective sleeve can comprise a tubular layer with an inner layer for engaging or contacting the skin about the affected portion of the patient. The tubular layer can comprises an elastic fabric layer comprising polyester-type fabric and/or a LYCRAT™-type stretchable fabric comprising SPANDEX™ or elastane fabric comprising polyurethane. The outer protective sleeve can substantially annularly surround the resilient layer and elastomeric layer. The end sections of the outer cover can be circular or disc-shaped. The strap can extend outwardly of and be secured to the outer cover.

In a preferred process (method) for constructing a medical device for removal of excess fluids from body tissue, a composite multilayered assembly can be formed for compressing body tissue of a patient in a controlled and graduated manner, by cutting a composite outer elastic fabric layer to a particular size and shape. A composite inner elastic fabric layer is cut to a similar size and shape as the composite outer elastic fabric layer. All but one pair of the corresponding edges of the composite inner elastic fabric layer and composite inner elastic fabric layer are secured together, such as by stitching, sewing, bonding, sonic welding, sealing, or fastening with VELCRO™-type fasteners, snaps, buttons, or zippers, to form a temporary pocket with an inlet opening positioned (disposed) between the pair of unsecured corresponding edges of the composite elastic fabric layers.

In the process for constructing a medical device, an elastomeric layer can be cut to a slighter smaller size and shape than each of the composite elastic fabric layers. A resilient layer can be cut into pieces of elastomeric components, such as foamed chips, foamed pieces, foamed parts, foamed sections, cut foam, or chopped foam, by shearing, chopping, slicing, and/or separating the resilient layer. Preferably, each of the elastomeric components are cut to have a maximum span smaller than the elastomeric layer and each of composite elastic fabric layers. The elastomeric components (e.g. chopped foam) can be arranged to form an array, series, set, matrix, or pattern of the elastomeric components on the resilient layer, while spacing the elastomeric components apart from each other to form channels or canals between the elastomeric components to enhance flow of excess fluid from the body tissue of the patient. The elastomeric components (e.g. chopped foam) can be glued, bonded or otherwise secured to the elastomeric layer to form flexible intermediate layers. The flexible intermediate layers can then be fully and entirely inserted through the inlet opening into the temporary pocket of the composite elastic fabric layers so that the flexible intermediate layers are positioned between the composite elastic fabric layers. Thereafter, the remaining unsecured edges of the composite elastic fabric layers are secured together, such as by stitching, sewing, bonding, sonic welding, sealing, or fastening with VELCRO™-type fasteners, snaps, buttons, or zippers, to close the temporary pocket.

In the process for constructing a medical device, the composite inner elastic fabric layer preferably has a lower denier and smaller thread thickness and more stretch than the composite outer elastic fabric layer and can be positioned to engage or contact the skin about the affected portion of the body of a patient. Each of the composite elastic fabric layers can be provided with a composition comprising a polyester-type fabric and a LYCRA™-type stretchable fabric comprising SPANDEX™ or elastane fabric comprising polyurethane and polyethylene glycol.

In one preferred embodiment of the process for constructing a medical device, a gradient pressure compression device can be formed with some of the elastomeric components (e.g. chopped foam) having a different density, size and/or shape than other elastomeric components. Zones of gradient pressure can be created and formed with the elastomeric components (e.g. chopped foam) in the medical device to help remove excess fluid from the tissue of the affected portion of the body of the patient. The gradient pressure compression device can enhance uniform distribution of compression about the affected portion of the patient.

In the process for constructing a medical device, a compressed portion can also be formed about an opening (e.g. hole), V-shaped notch, V-shaped extension and/or protuberance for accommodating and receiving the affected portion of the body of the patient, such as a joint, shoulder, knee, elbow, ankle, foot, at least one toe, at least one finger, a hand, wrist, upper arm, lower arm, thigh, chest, stomach, back, upper leg, and lower leg.

The process for constructing a medical device can further include stitching the medical device with stitches of varying lengths to provide different amounts of stretch to different portions (sections) of the medical device. The stitches can include longer stitches for allowing the inner and outer layers to more comfortably conform to the body of the patient as the patient moves to help maintain constant compression and facilitate removal of excess fluid from the affected portion of the body of the patient. The stitches can also include shorter stitches for less stretch and a tighter fit of the medical device about the affected portion of the patient for helping prevent slippage of the medical device during wear of the medical device by the patient as well as for facilitating channeling and removal of excess fluid away from the affected portion of the patient.

A more detailed explanation of the invention is provided in the following detailed descriptions and appended claims taken in conjunction with the accompanying drawings.

BRIEF DESCRIPTION OF THE DRAWINGS

FIG. 1 is an assembly or exploded view of one embodiment of the medical device in accordance with principles of the present invention.

FIG. 2 is a perspective view of a portion of the medical device during construction of the medical device.

FIG. 3 is a front view of a further portion of the medical device during construction of the medical device.

FIG. 4 is an assembly or exploded view of the further portion of the medical device during construction of the medical device.

FIG. 5 is a perspective view of other portions of the medical device during construction of the medical device.

FIG. 6 is a front view of another embodiment of the medical device in accordance with principles of the present invention.

FIG. 7 is a front view of a further embodiment of the medical device in accordance with principles of the present invention.

FIG. 8 is a front view of still another embodiment of the medical device in accordance with principles of the present invention.

FIG. 9 is a perspective view of a medical device for receiving a finger or digit of a patient in accordance with principles of the present invention.

FIG. 10 is a perspective view of a medical device for receiving a thumb of a patient in accordance with principles of the present invention.

FIG. 15 is a perspective view of a cylindrical type or style medical device about the stomach or chest of a patient in accordance with principles of the present invention.

FIG. 16 is an enlarged perspective view of the cylindrical type or style medical device of FIG. 15.

FIG. 17 is a perspective view of a medical device for receiving a portion of an arm near an elbow of a patient which is especially useful for treating tendonitis in accordance with principles of the present invention.

FIG. 18 is a perspective view of the medical device in a closed position for receiving a thumb of a patient in accordance with principles of the present invention.

DETAILED DESCRIPTION OF THE INVENTION

Figure 11:
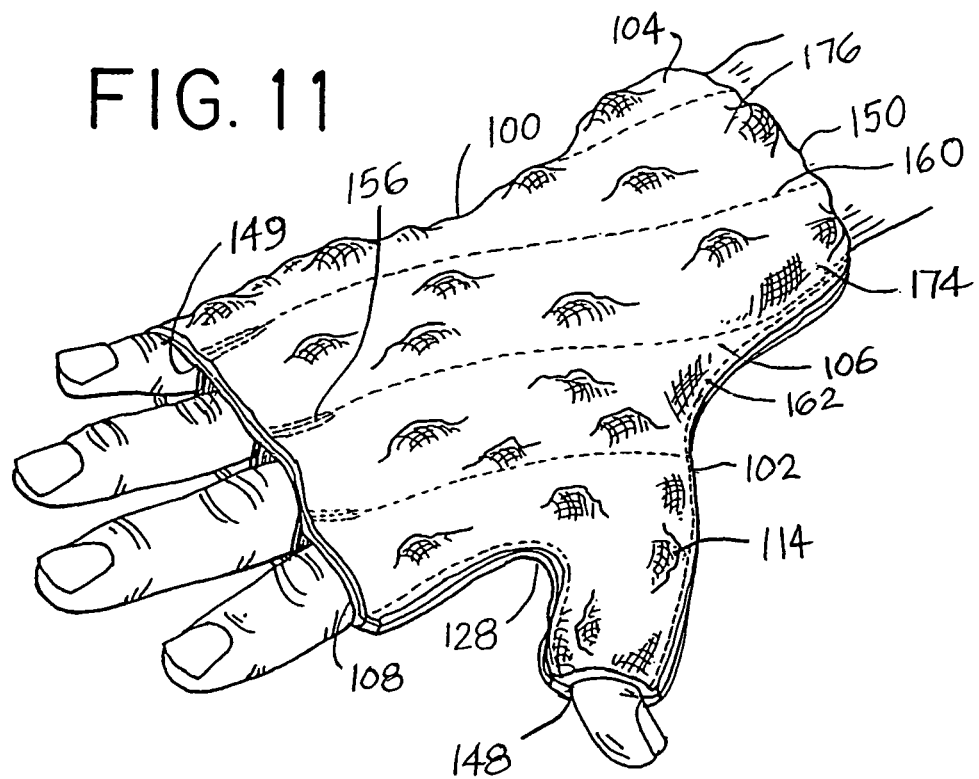
FIG. 11 is a perspective view of a medical device for receiving a hand of a patient in accordance with principles of the present invention.

The following is a detailed description and explanation of the preferred embodiments of the invention and best modes for practicing the invention.

A medical device 100 (FIG. 1) can be constructed and assembly for removal of excess fluids from body tissue and is particularly useful to treat soft tissue inflammation, damage, edema and/or lymphedema. Advantageously, the medical device comprises a composite multilayered assembly 102 that provides a gradient pressure compression device 104 to compress body tissue of a patient in a controlled and graduated manner. The composite multilayered assembly can have an outer layer 106 and an inner layer 108 which cooperate with each other to enhance uniform distribution of compression about the affected portion (area) of the patient. The inner layer is positioned to engage or contact the skin about an affected portion of the body of a patient and has a lower denier, thinner thread thickness and more stretch than the outer layer. The inner and outer layers can comprise elastic fabric layers with a polyester-type fabric and a LYCRA™-type stretchable fabric comprising SPANDEX™ or elastane fabric with polyurethane and/or polyethylene glycol. Preferably, the inner layer has a lower denier than the outer fabric to more comfortably contact or cushion the skin about the affected portion of the patient.

The composite multilayered assembly 102 (FIG. 1) also comprises flexible intermediate layers 110 and 112 that are positioned between the outer and inner layers 106 and 108. The flexible intermediate layers can comprise an elastomeric layer 110 and a resilient layer 112 having a different composition and structure than the inner and outer layers. The elastomeric layer can be made of foam material and is preferably flexible to conform to the affected portion of the body of the patient. The resilient layer can comprise an array, series, set, matrix, pattern, and plurality of elastomeric components 114, such as foamed chips, foamed pieces, foamed parts, foamed sections, cut foam, and/or chopped foam, that are secured to the elastomeric layer. Preferably, at least some of the elastomeric components (e.g. chopped foam) have a different density and/or size and/or shape than the other elastomeric components in the medical device. In the preferred form, the elastomeric components (e.g. chopped foam) are spaced apart from each other to form channels (canals) 116 therebetween to enhance flow of excess fluids from the body tissue of the patient. The channels or canals create zones of gradient pressure to help move excess fluid from the tissue of the affected portion of the body of the patient. Each of the elastomeric components (e.g. chopped foam) can have a maximum span and size that is smaller than the elastomeric layer, outer layer, and inner layer. The inner layer can facilitate penetration of the elastomeric components (e.g. chopped foam) against or into the soft issue of the affected portion of the body of the patient.

The composite multilayer assembly provides a unit that can be made of four (4) layers 106-112 (FIG. 1) of different materials. The outer layer 106 can be a fabric comprised of a combination of LYCRA™ fabric and polyester in variable percentages (or a similar material) with a high dernier factor. The outer layer is useful to apply pressure to layers 108, 110, and 112. Compression can be increased by cutting out strips and sewing the edges together; the smaller the body part that the unit is intended for (ankle versus, thigh, wrist versus. upper arm, etc.), the smaller the cut outs have to be. Additionally, the larger the body part that the unit is intended for, the more cut outs can be utilized. Layer 110 can be ¼ (0.25) inch thick sheet of LATEX™ fabric (or a similar material) that is flexible enough to conform to the human body. Glue can be applied to the inner surface of layer 110 so that chopped foam of various densities will adhere. Layer 112 can be comprised of foam of various densities that have been chopped to specific sizes, depending on their placement on the unit. Inner layer 108 can be a fabric comprised of a combination of LYCRA™ and polyester in variable percentages (or a similar material) with a lower dernier factor than outer layer 106. In contrast to the outer layer 106, the lower dernier factor of inner layer 108 allows deeper penetration of the chips into the soft tissue of the body part, while receiving the distributed pressure from the high dernier factor fabric of outer layer 106.

The purpose of the layers 106-112 (FIG. 1) of the composite multilayered assembly of the medical device is as follows. The outer layer 106, with its higher dernier factor, can be useful to force pressure down through the subsequent layers. Layer 110 can be useful to distribute the pressure being applied by the outer layer to the foam chips 114 of layer 112. The layer 112 can create various regions of high and low pressure (high pressure areas are formed where the foam pieces are pressed against the body and low pressure areas are formed where the foam pieces are not pressed against the body). The density and placement of the foam pieces can vary according to amount of pressure desired in specific areas of the unit providing the medical device. The proper arrangement of the foam pieces helps to create zones of gradient pressure that move excess body fluids away from affected areas to other parts of the body where the fluids can be processed through waste. The inner layer 108 is useful to close the unit internally (protecting the foam chips from being torn off) and to provide a comfortable surface which lies against the body. The inner layer preferably comprises a fabric with a low dernier factor help to allow the foam chips to press into the body tissue as much as possible.

The composite multilayered assembly 102 (FIG. 1) of the medical device can be assembled as follows. The inner layer 108 can be laid flat on a table. The outer layer 106 can be placed on top of the inner layer. On both layers 106 and 108, the smooth side of the material is oriented so that they face each other. At this point, the measurements for the unit (based on the shape of the body part the unit is intended for) can be used to draw its shape. Several measurements can be used, both in height (length of body part) and circumference, for example, an arm unit has a basic design with proportions that are adjusted for bodies of different sizes. All sides on the inner and outer layers can be turned to the inside to assure edges are smooth. Ultrasonic welds can be used after the layout is complete to seal all the edges except one. Scrap material can be removed, leaving the inner and outer layers joined as a single piece.

The flexible intermediate layers 110 and 112 (FIG. 1) can be constructed in the following way. Glue can be applied to one surface of layer 110 and then chopped foam pieces 114 of layer 112 are placed onto layer 110 according to their density (which affects the amount of pressure it will exert on the body tissue and the direction of gradient pressure that is desired to move the body fluid). Next, the composite inner and outer layers 106 and 108 can be used as a pattern to cut out an identical shape in composite flexible intermediate layers 110 and 112. Layers 106 and 108 can be placed over layers 110 and 112 and its outline can be traced and then cut out. Once that is done, the composite flexible intermediate layers 110 and 112 can be rolled and inserted into partially secured composite inner and outer layers 106 and 108 through its unsealed edge, oriented so that the inner and outer layers 106 and 108 are facing each other and the flexible intermediate layers 110 and 112 are facing each other. Then the flexible intermediate layers 110 and 112 can be unrolled within the inner and outer layers 106 and 108 and allowed to lay flat and the remaining open edge of the inner and outer layers 106 and 108 can be finally sealed. In cases where the unit is intended to be used as a sleeve-type device which surrounds the affected body part, the outer edges of the inner and outer layers 106 and 108 can be joined, creating a tube-like unit with the layer 106 facing out and layer 108 facing in.

As shown in FIGS. 2-5, the basic composite multilayered assembly 102 of the medical device 100 can be varied as follows. For some designs or embodiments of the invention, a strip of light dernier fabric 118 and 120 can be sewn to both the outer and inner layers 106 and 108 to create a case (casing) 122 for the foam insert (layers 110 and 112 and/or individual chopped foam pieces 116, depending on the design of the medical device). The casing walls 124 can be made of either separate fabric strips which are sewn together, or a single strip of fabric cut to the shape of the pattern of the medical device. The addition of a casing wall can allow for an even distribution of variegated pressure (from the foam chips 114 and the zero-pressure or lower pressure canals 116) around the entire limb and/or affected portion (area) of the patient when the medical device is completely assembled. Preferably, the walls of opposing sides are joined face to face, rather than by their edges only.

As shown in FIGS. 3-4, light denier fabric can be cut out for the inner layer 108 and heavier denier fabric can be cut out for the outer layer 106. The assembled composite layer assembly unit 102 (FIG. 5) can have cut out strips creating a wall 124 around it. The composite of comprises flexible intermediate layers 110 and 112 and/or individual foam pieces 114 can be inserted into the casing 122. When assembled and constructed, the medical device can have a casing with casing walls that provides a case or periphery which is positioned peripherally about at least a portion of the flexible intermediate layers to help facilitate even distribution of variegated pressure from the elastomeric components (e.g. chopped foam) and the channels or cannels about the affected portion of the body of the patient.

The medical device can provide many features including a unit that can be constructed of four distinct layers 106-112 (FIGS. 1-5). Each layer has a specific function and can compress the body tissue of the patient in a controlled and graduated manner. The differences in the denier factor between the outer and inner layers 106 and 108 can create stronger, more evenly distributed compression. Lower resistance fabric in the inner layer 108 can allow the foam chips (foam pieces) 114 to press deeper into the affected area of the patient. Foam pieces 114 of varying density can be glued to the surface of the unit's inner layer 110. When constructed, the foam typically remains in place without undesired gaps or overfilled areas. The foam pieces can be arranged in graduated patters of higher or lower density. Foam pieces of specific densities can be used exclusively in certain areas of the medical device to achieve zones of high or lower pressure against the body tissue. The use of foam with a range of densities can work in combination with the compression from the outer layer 106 to provide pressure which helps stimulate fluid movement of the patient. The material used in the outer layer 106, combined with its design, help forces pressure down the other layers 108-112 or unit's sub-layers. Pleats, such as 126 (FIG. 10), or seams, such as 128 (FIGS. 9-14) and/or one or more zippers, buttons, stitches or other fasteners 160 and 162, can be sewn in the outer layer 106 to help selectively increase pressure in specific areas of the medical device (unit). The number of pleats, seams, zippers, buttons, stitches, or fasteners, can vary depending on the design, shape, and/or total area of the outer layer or other layers and the pressure to be applied. If desired, the pleats can be sewn into one or more of the other layers 108-112.

As shown in FIG. 6, rows of radiating straight lines 130 can be sewn into the medical device (unit) 100 to augment the gradient pressure created by the foam to help move excess fluids away from the affected area of the patient. The lines 130 can be oriented along the length of the unit and can be tapered so they are closer at the bottom or one end of the medical device and spread further apart at the top or the other end of the medical device. These lengthwise rows of tapered lines connect to a pair of intersecting or shorter angled rows of lines 132-133 that can be tapered, as well, and guide the excess fluid into the body's waste system.

Due to differences in the shape and structure of various parts of the body, an alternate design can be used to achieve fluid movement in some cases. Individual, tapered channels (canals) 134 (FIG. 7) that can be oriented along the length of the medical device (unit) can be placed between stacks of horizontal rows of tapered lines 136-137. The area or space between the vertical or longitudinal rows of tapered lines 138-139 can be devoid of foam chips, while spaces or area between the horizontal rows of tapered lines 136-137 retain them, to creates a canal (channel) 134 of zero or low pressure that accepts the fluid coming from the gradient pressure of the horizontal rows of tapered lines 136-137 and moves it quickly up the length and/or along the medical device (unit) and away from the affected area of the body.

As discussed above, the medical device can further have one or more converging or diverging sections 130-139 (FIGS. 6-7) with curved or substantially straight tapered lines or tapered channels for augmenting gradient pressure and enhancing flow of excess fluid away from the affected portion of the body of the patient. The tapered lines can include longitudinally extending tapered lines 130, 138, or 139 and/or laterally extending tapered lines 132, 133, 136, and/or 137. The tapered channels or canals can include at least one longitudinally extending tapered channel (cannel) 130 or 134 and/or at least one laterally extending tapered channel (canal) 140 and/or 142.

As shown in FIG. 8, one or more V-shaped notches 144 can be cut out of the assembled composite material providing the composite multilayered assembly 102 of layers 106-112 and/or V-shaped extensions (protuberances) 146 can be cut out of the assembled composite material providing the composite multilayered assembly 102 of layers 106-112, to help the unit conform to specific joints (such as the shoulder, knee, elbow and ankle) without a loss of pressure. Furthermore, the medical device can provide a compressed portion with one or more openings (holes) 148-155 (FIGS. 9-14) or V-shaped notches 144 (FIG. 8) and/or one or more V-shaped extension 146 (FIGS. 2-8) or other protuberance for accommodating and receiving the affected portion of the body of the patient, such as a joint, shoulder, knee, elbow, ankle, foot, at least one toe, at least one finger, hand, wrist, upper arm, lower arm, thigh, chest, stomach, back, upper leg, and lower leg.

The medical devices 100 (FIGS. 11-12) for the hands and feet can utilize elastic bands 156 between the digits (fingers or toes) to provide compression to each individually. The elastic bands can minimize or avoid empty spaces between the digits and help provide contact with the chopped foam 114 of varying densities. More particularly, the medical device can comprise a hand-shaped or foot-shaped medical device with elastic bands sewn or secured between digits of the medical device about the fingers or toes of the patient to enhance pressure from the elastomeric components (e.g. chopped foam) to further assist in removing excess fluid away from the affected portion of the patient.

The back of the hand and/or top of the foot also benefit from the medical device. Compression can be maintained to the very edge of the medical device and graduated pressure can be introduced by incorporating the previously mentioned methods (strategically placed chopped foam of varying density and sewn-in, radiating lines to create zones of zero or lower pressure). These elements can all work together to remove excess fluid from the entire hand and/or foot.

In contrast to prior medical devices, where only one length of stitch has been used to sew and join its various components, the new medical device 100 (FIGS. 9-17) can have a combination of stitches 160 and 162 of varying lengths to provide different amounts of stretch in different parts of the medical device. Longer stitches 160 allow the materials of the outer and inner layers 106 and 108 to conform better to the patient's body as the body moves in order to help keep the compression consistent, uniform, and/or constant and facilitate faster reduction or removal of excess fluid from the affected area of the patient. Since the joints and seams are more flexible, this also makes the fit more comfortable to the patient, which increases compliance. Conversely, shorter stitches 162 can be utilized in specific areas to create zones where the fit is tighter and there is less stretch to the medical device. This augments the channeling technique of pushing excess fluid into the zero or lower pressure canals (channels) and helps move excess fluid away from the swollen area. This also helps to focus or concentrate pressure on areas of the body that are difficult to treat, such as crevasses. Furthermore, the shorter stitch allows the creation of "lock spots" where the fit is tight enough to help prevent slippage of the medical device, in general. For example, a tighter fit around the elbow will help keep the medical device situated properly and inhibit drift due to gravity or the patient's movement. More specifically, the medical device can have an outer and/or inner layer with stitches 160 and 162 of varying lengths to provide different amounts of stretch to different portions (sections) of the medical device. The stitches can include longer stitches 160 for allowing the inner and outer layers to more comfortably conform to the body of the patient as the patient moves to help maintain constant compression and facilitate removal of excess fluid from the affected portion of the body of the patient. The stitches can also include shorter stitches 162 for less stretch and a tighter fit of the medical device about the affected portion of the patient for helping prevent slippage of the medical device during wear of the medical device by the patient and for facilitating channeling and removal of excess fluid away from the affected portion of the patient.

The medical device 100 of FIG. 9 comprises a single digit-receiving medical device (digit-shaped medical device) 166 for receiving and helping remove excess fluid away from an affected portion (area) of a digit, such as finger or toe, of a patient. The single digit-receiving medical device is general tubular with a central opening 148 to receive and surround the digit of the patient. The single digit-receiving medical device 166 can have one or more of the features described with respect to the medical device of FIGS. 1-8.

The medical device 100 of FIG. 10 comprises an isolated thumb-receiving medical device (thumb-shaped medical device) 168 for receiving and helping remove excess fluid away from an affected portion (area) of a thumb of a patient. The isolated thumb-receiving medical device can have a thumb-receiving central opening 148 to receive and surround the thumb of the patient. The isolated thumb-receiving medical device can have a wrist-receiving portion 170 with a wrist-receiving opening 150 to receive and surround the wrist of the patient. The isolated thumb-receiving medical device can also have a wrist band 172, such as made of a VELCRO™-type material, which can be sewn or otherwise secured to the wrist-receiving portion of the isolated thumb-receiving medical device, to adjust, tighten, and secure the wrist-receiving portion of the isolated thumb-receiving medical device to and/or about the hand and/or wrist of the patient. The isolated thumb-receiving medical device 168 can have one or more of the features described with respect to the medical device of FIGS. 1-8.

The medical device 100 of FIG. 11 comprises a hand-receiving medical device (hand-shaped medical device) 174 providing a medical glove 176 for receiving and helping remove excess fluid away from an affected portion (area) of a hand of a patient. The hand-receiving medical device (medical glove) has finger-receiving openings 149 to receive and surround the fingers of the patent and has a wrist-receiving opening 150 to receive and surround the wrist of the patient. As discussed above, the hand-receiving medical device (medical glove) can have elastic bands 156 that are sewn or otherwise secured between digits of the hand-receiving medical device about the fingers of the patient to enhance pressure from the elastomeric components 114 (e.g. chopped foam) to further assist in removing excess fluid away from the affected portion of the hand of the patient. The hand-receiving medical device (medical glove) can have one or more of the features described with respect to the medical device of FIGS. 1-8.

Figure 12:
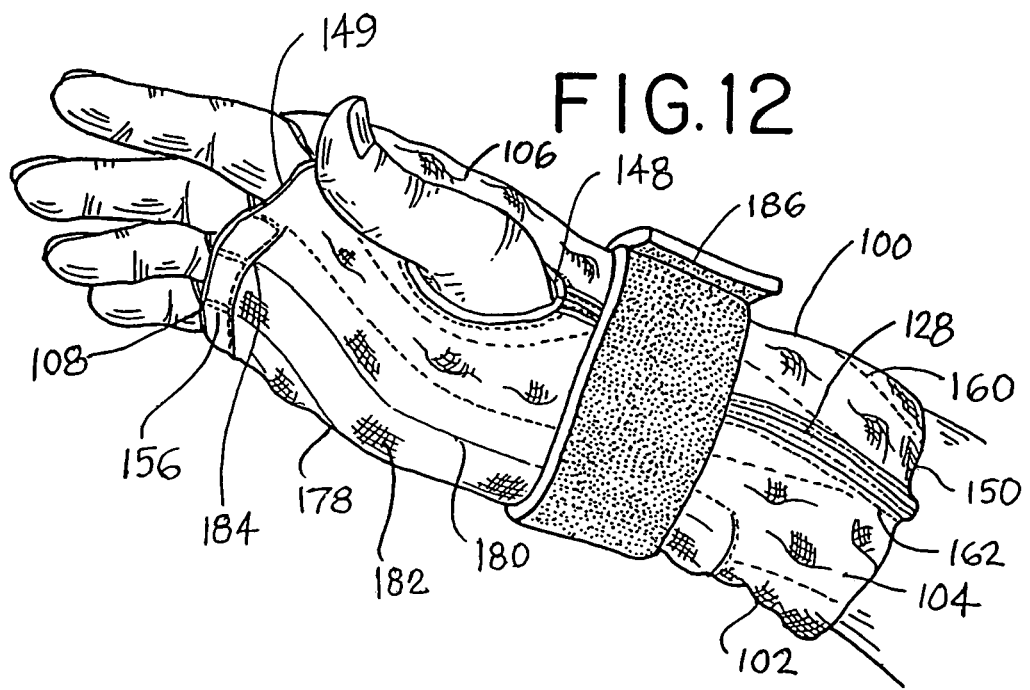
FIG. 12 is a perspective view of a medical device with a splint for receiving a hand of a patient in accordance with principles of the present invention.

As shown in FIG. 12, the medical device 100 can also provide a splinted medical assembly (splinted medical device) 178. In the splinted medical assembly, a splint 180 is secured to the medical device and a fabric overlay 182 is sewn (stitched) or otherwise secured to the medical device over the splint. The fabric overlay cooperates with the splinted medical assembly (splinted medical device) to provide a pocket 184 for receiving the splint. The pocket and the splinted medical assembly (splinted medical device) cooperate with each other to allow lateral movement of the splint so as to accommodate movement of a patient's fingers, toes or other body portion that extends from the splint, as well as reduce stiffness of the affected portion of the body and enhance removal of excess fluid form the affected portion of the body of the patient. The splinted medical assembly (splinted medical device) can also have a wrist band 186, such as made of a VELCRO™-type material, to adjust, tighten, and secure the splinted medical assembly (splinted medical device) to the hand, wrist, or other body part of the patient. The splinted medical assembly (splinted medical device) can have one or more of the features described with respect to the medical device of FIGS. 1-8.

For example, in cases where the hand and wrist need to be maintained in a relatively fixed position for the treatment of certain conditions, a hard splint 166 (FIG. 12) can be positioned or introduced into the splinted medical assembly (splinted medical device) 178. There are two unique design features to the splint's attachment: (1) the splint can be attached to the device at two points on each side at the base of the splint (away from the hand); (2) a section of fabric is sewn on the outside of the device, over the already-attached splint, creating a closed pocket 184 around the splint. These design features work together to allow lateral movement of the splint and, therefore, lateral movement of the hand, providing greater comfort to the patient, while maintaining the hand, wrist and forearm in a relative fixed position, reducing stiffness and aiding in the flow of fluids through the treated area.

Figure 13:
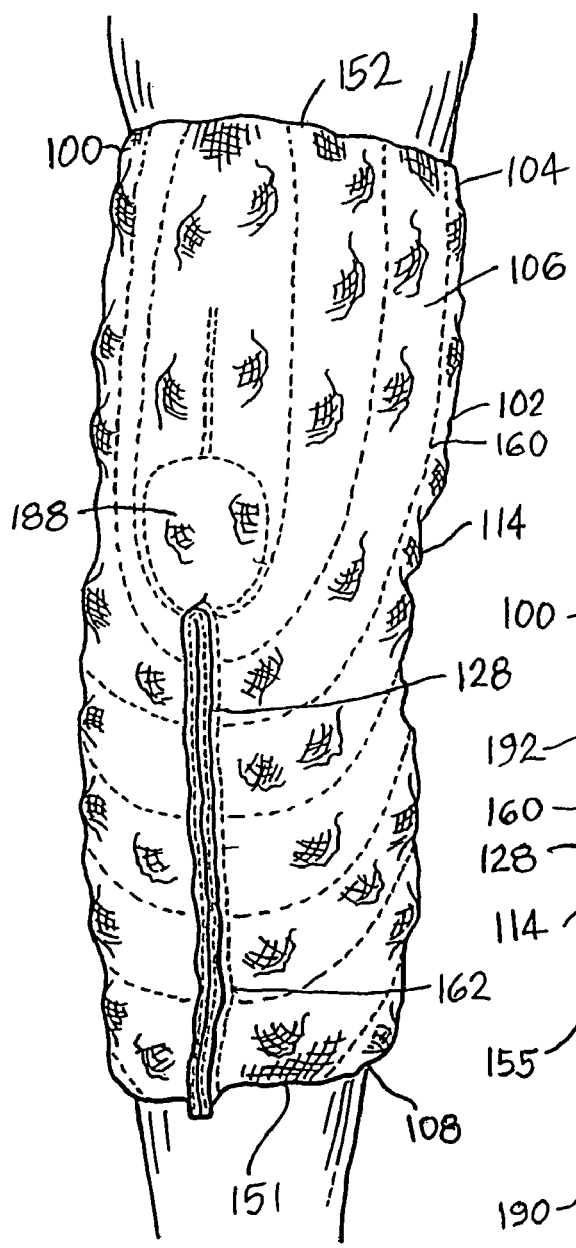
FIG. 13 is a perspective view of a medical device for receiving a knee and leg or elbow and arm of a patient in accordance with principles of the present invention and showing portion broken away for ease of understanding and illustration.

The medical device 100 of FIG. 13 comprises a knee-receiving medical device (knee-shaped medical device) 188 for receiving and helping remove excess fluid away from an affected portion (area) of the knee and leg of a patient. The knee-receiving medical device is general tubular with a central elongated opening 151 and 152 to receive and surround the knee and a portion of the leg of the patient. The knee-receiving medical device 188 can have one or more of the features described with respect to the medical device of FIGS. 1-8.

The medical device 100 of FIG. 13 can also comprise an elbow-receiving medical device (elbow-shaped medical device) 188 for receiving and helping remove excess fluid away from an affected portion (area) of the elbow and arm of a patient. The elbow-receiving medical device is general tubular with a central elongated opening 151 and 152 to receive and surround the elbow and a portion of the arm of the patient. The elbow-receiving medical device 188 can have one or more of the features described with respect to the medical device of FIGS. 1-8.

Figure 14:
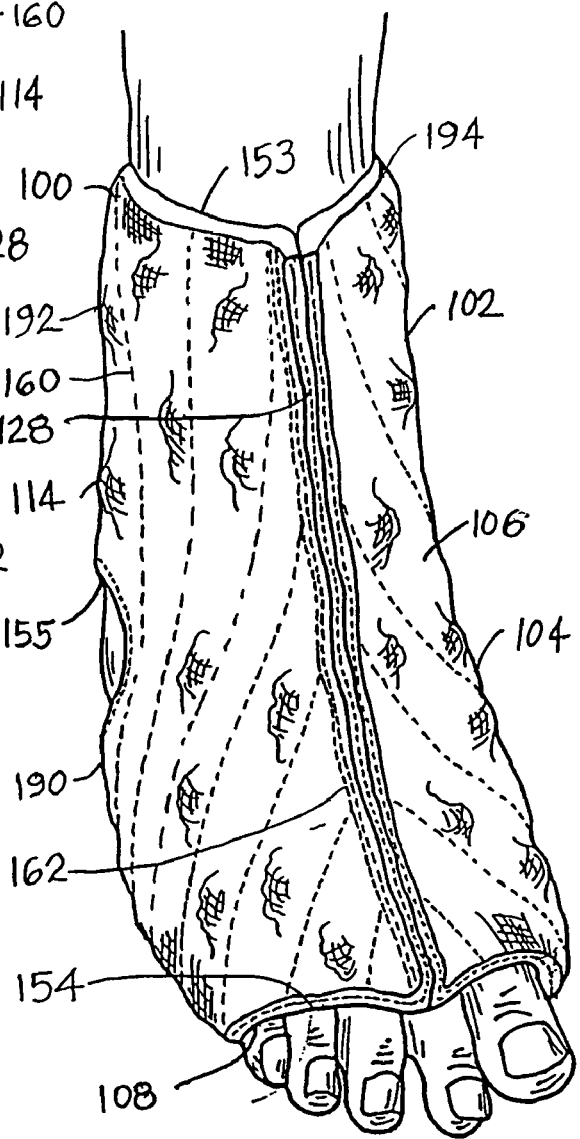
FIG. 14 is a perspective view of a medical device for receiving an ankle and foot of a patient in accordance with principles of the present invention.

The medical device 100 of FIG. 14 comprises a foot-receiving medical device (foot-shaped medical device or ankle-receiving medical device) 190 which provides a medical boot 192 for receiving and helping remove excess fluid away from an affected portion (area) of the ankle and foot of a patient. The foot-receiving medical device has a general tubular portion 194 with a central elongated opening 153 to receive and surround a lower portion of the leg, a foot-receiving opening 154 to receive and surround the foot of the patient, and an ankle-receiving opening 155 to receive the ankle of the patient. The foot-receiving medical device (ankle-receiving medical device) 190 can have one or more of the features described with respect to the medical device of FIGS. 1-8.

As shown in FIGS. 15-16, the medical device comprises a cylindrical type or style medical device 196 with a composite multilayered cylindrical type or style assembly 198 for removal of excess fluids from body tissue of a patient and/or for treatment of large lymphoceles or lymphocytes and conditions where excess body fluid can cause skin folding or softening of fibrous tissue. The composite multilayered cylindrical type or style assembly has flexible layers including an elastomeric layer 108 comprising a central core and a resilient layer 112 secured to the elastomeric layer. Elongated strapping 200 comprising at least one strap 202, which can be nylon webbing or fabric, or a VELCRO™-type fabric, extends across the elastomeric layer to enhance isometric pressure of the cylindrical medical device. The strap can have a buckle 204 and end portions 206 and 208 that can be buckled, tied or otherwise secured about the trunk, chest, stomach, back of other affected portion (area) of the body of the patient. The strap can also have an intermediate portion 210 that can be positioned between and integrally connected to the end portions of the strap and/or extend through the cylindrical medical device.

The elastomeric layer 110 (FIGS. 15-16) in the cylindrical type or style medical device 196 can be made of a foam material and is preferably flexible to conform to the affected portion of the body of the patient. The resilient layer 112 in the cylindrical medical device can comprise an array, series, set, matrix, pattern, and plurality of elastomeric components 114, such as foamed chips, foamed pieces, foamed parts, foamed sections, cut foam, and/or chopped foam; that are secured to the elastomeric layer. Some of the elastomeric components (e.g. chopped foam) in the cylindrical medical device can have a different density and/or size and/or shape than the other elastomeric components in the cylindrical medical device. Desirably, the elastomeric components (e.g. chopped foam) in the cylindrical medical device are spaced apart from each other to form channels (canals) 116 therebetween to enhance flow of excess fluids from the body tissue of the patient. Each of the elastomeric components (e.g. chopped foam) in the cylindrical medical device can have a maximum span and size that is smaller than the elastomeric layer and outer cover (shell) 212 that can provide an outer layer and/or inner layer. Significantly, the elastomeric components (e.g. chopped foam) of the cylindrical medical device cooperate with each other to provide micro-zones of high and low pressure to facilitate movement of excess fluid away from the affected area or skin folds of the body of the patient.

The composite multilayered cylindrical assembly 198 (FIGS. 15-16) of the cylindrical type or style medical device 198 can have an outer cover 212 that can comprise a shell. The outer cover also provide a curved arcuate inner layer 108 that contact the affected portion (area) of the body of the patient and a curved arcuate outer layer 106 that is positioned away from the affected portion of the body of the patient. Preferably, the outer cover has a different composition and structure than the elastomeric layer and the resilient layer and is larger than the elastomeric components (e.g. chopped foam). The outer cover can provide an outer protective sleeve 214 which are sewn by stitches 162 or otherwise secured to axially opposite circular end sections 216 and 218. The outer protective sleeve can comprise a tubular layer with an inner portion (layer) 106 for engaging or contacting the skin about the affected portion of the patient. The tubular layer can comprises an elastic fabric layer comprising polyester-type fabric and/or a LYCRA™-type stretchable fabric comprising SPANDEX™ or elastane fabric comprising polyurethane. The outer protective sleeve can substantially annularly surround the resilient layer and elastomeric layer, as well as the intermediate portion of the strapping. The end sections 216 and 218 of the outer cover can be circular or disc-shaped and can have central longitudinal slots 220 that provide passageways for passage of the end portions of the strap so that the end portions of the strap extend outwardly of the outer cover.

The cylindrical type or style medical device 196 (FIGS. 15-16) can be used for the treatment of large lymphoceles and conditions where excess body fluid causes skin folding, as well as for the softening of fibrotic tissue. The unit can be constructed using the following materials: a ¼ (0.25) inch thick sheet of foam 110 or a similar material, cut into a rectangular shape; chopped foam chips 114 of a certain density in varying shapes and sizes; strapping 200 comprising a material such as nylon webbing with high tensile strength and very low stretch; and a outer shell (outer layer) 212 comprising a fabric of LYCRA™-type fabric and polyester (or a similar material) with a low dernier factor.

The cylindrical type or style medical device 196 (FIGS. 15-16) can be constructed and assembled as follows. In step 1, glue is applied to the entire surface of the flat foam sheet 110. Strapping material 200 is placed on one edge and adhered. Beginning with the edge with the strapping material, the foam sheet is then tightly rolled to create a cylindrical shape, so that the strap 202 is in the center, with ample length extending out from either side. In step 2, glue is applied to the outer surface of the cylindrical shape. Chopped foam chips 114 are applied to the outer surface, covering it entirely with non-uniformly sized pieces. In step 3, a sleeve 214 made of a fabric with a low dernier factor can sewn around the cylindrical device to enclose the foam chips and provide a smooth surface against the skin. In step 4, the strapping material 200 is cut to desired length and a clasp (buckle) 204 or other mechanism to close the loop can be attached to the strap.

In the cylindrical type or style medical device 196 (FIGS. 15-16), the rolled foam sheet 110 provides a central core to the medical device, which helps produce a consistent pressure when applied to areas where excess fluid has created large lymphoceles, skin folds, and fibrotic tissue. The chopped foam pieces 114 of varying sizes and shapes create numerous micro-zones of high and low pressure that stimulate the movement of excess fluid away from the affected area to other parts of the body where the fluids can be processed through waste. The foam pieces 114 around a cylindrical medical device allows for greater surface area coverage in difficult to treat areas such as skin folds. Also, the strapping material 200 can extend through the core of the medical device to help enhance isometric pressure against the affected portion (area) of the body of the patient. The outer fabric sleeve 214 provides a comfortable surface which lays against the body, as well as protection for the foam chips from being torn off. A fabric with a low dernier factor is helpful for the outer sleeve 214 to allow the foam chips 114 to press into the body tissue of the patient as much as possible.

The medical device 100 of FIGS. 17-18 comprises an arm-receiving medical device 222 providing a tendonitis-relieving medical device for receiving and helping remove excess fluid away from an affected portion (area) of an arm (lower arm or upper arm) near an elbow of a patient which is especially useful for treating tendonitis. The arm-receiving medical device (tendonitis-relieving medical device) can have an elbow or arm-engaging portion 224 that contacts and engages the affected portion (area) of the patient. One or more arm bands (straps) 226, such as made of a VELCRO™-type material, can be sewn or otherwise secured to the elbow or arm-engaging portion to adjust, tighten, and secure the arm-receiving medical device (tendonitis-relieving medical device) to and/or about the elbow and/or adjacent arm portion of the patient. The arm-receiving medical device (tendonitis-relieving medical device) can have a clasp (buckle) 228 to facilitate tightening, closing and locking of the arm band (strap). The arm-receiving medical device (tendonitis-relieving medical device) can have one or more of the features described with respect to the medical device of FIGS. 1-8.

Among the many advantages of the medical device and process (method) can be:

1. Superior product and apparatus for enhanced treatment soft tissue inflammation, damage, edema and/or lymphedema.
2. Outstanding performance.
3. Superb removal of excess fluids from body tissue.
4. Excellent treatment of tendonitis.
5. Better treatment of large lymphoceles or lymphocytes and conditions where excess body fluid can cause skin folding or softening of fibrous tissue or fibrotic tissue.
6. Patient friendly.
7. Reliable.
8. Readily transportable.
9. Light weight.
10. Portable.
11. Comfortable.
12. Easy to use and wear.
13. Durable
14. Economical.
15. Attractive.
16. Efficient.
17. Effective.

Although embodiments of the invention have been shown and described, it is to be understood that various modifications, substitutions, and rearrangements of parts, components, and/or process (method) steps, as well as other uses, shapes, construction, and design of the medical device can be made by those skilled in the art without departing from the novel spirit and scope of this invention.

What is claimed is:

1. A medical device for removal of excess fluids from body tissue, comprising:
   a composite multilayered assembly for compressing body tissue of a patient in a controlled and graduated manner, said composite multilayered assembly having
   an outer layer;
   an inner layer for engaging or contacting the skin about an affected portion of the body of a patient, said inner layer cooperating with said outer layer to enhance uniform distribution of compression about the affected portion of the patient; and
   flexible intermediate layers positioned between said outer layer and said inner layer, said flexible intermediate layers comprising
   an elastomeric layer having a different composition and structure than said inner and outer layers, said elastomeric layer being flexible to conform to the affected portion of the body of the patient; and
   a resilient layer secured to said elastomeric layer, said resilient layer having a different composition and structure than said inner and outer layers, said resilient layer selected from the group consisting of an array, series, set, matrix, pattern, and plurality of discrete spaced elastomeric components, channels between said spaced elastomeric components on a surface of said resilient layer to enhance flow of excess fluids from the body tissue of the patient, and each of said elastomeric components having a maximum span smaller than said elastomeric layer and being smaller than said outer layer and said inner layer, a converging section defining substantially straight tapered lines, tapered channels, or tapered cannels for augmenting gradient pressure and enhancing flow of excess fluids away from the affected portion of the body of the patient;
   said tapered lines including longitudinally extending tapered lines and/or laterally extending tapered lines; and
   said tapered channels including at least one longitudinally extending, tapered channel and/or at least one laterally extending tapered channel.

2. A medical device in accordance with claim 1 comprising:
   a gradient pressure compression device; and
   said elastomeric components cooperating with each other for creating zones of gradient pressure to help move excess fluid from the tissue of the affected portion of the body of the patient.

3. A medical device in accordance with claim 1 wherein:
   said elastomeric components are selected from the group consisting of foamed chips, foamed pieces, foamed parts, foamed sections, cut foam, and chopped foam; and
   said inner layer facilitates penetration of the elastomeric components against or into soft issue of the affected portion of the body of the patient.

4. A medical device in accordance with claim 1 wherein at least some of said elastomeric components have a different density than other elastomeric components.

5. A medical device in accordance with claim 1 wherein said outer layer comprises a composite outer elastic fabric layer.

6. A medical device in accordance with claim 5 wherein said composite outer elastic fabric layer comprises a polyester-type fabric and a stretchable fabric comprising elastane fabric formed of polyurethane and polyethylene glycol.

7. A medical device in accordance with claim 1 wherein said inner layer comprises a composite inner elastic fabric layer with a resilient surface for comfortably contacting or cushioning the skin about the affected portion of the patient.

8. A medical device in accordance with claim 7 wherein said composite inner elastic fabric layer comprises by a polyester-type fabric and a stretchable fabric comprising or elastane fabric formed of polyurethane and polyethylene glycol.

9. A medical device in accordance with claim 1 wherein said outer layer comprises a high denier fabric of thick threads and said inner layer comprises a low denier fabric of thin threads with more stretch than said outer layer.

10. A medical device in accordance with claim 1 wherein:
    said composite multilayered assembly has sewn or sealed edges and a compressed portion about an opening, V-shaped notch, V-shaped extension and/or protuberance for accommodating and receiving the affected portion of the body of the patient; and
    said affected portion of the body is selected from the group consisting of a joint, shoulder, knee, elbow, ankle, foot, at least one toe, at least one finger, hand, wrist, upper arm, lower arm, thigh, chest, stomach, back, upper leg, lower leg, groin, genitals, neck, face, and head.

11. A medical device in accordance with claim 1 including casing walls providing a case or periphery positioned peripherally about at least a portion of the flexible intermediate layers for facilitating even distribution of variegated pressure from the elastomeric components and the channels about the affected portion of the body of the patient.

12. A medical device in accordance with claim 1 wherein said outer layer has pleats or seams.

13. A medical device in accordance with claim 1 for engaging or contacting the affected portion of a hand or foot of a patient, said medical device having elastic bands sewn or secured between digits about the fingers or toes of the patient to enhance pressure from the elastomeric components to further assist in removing excess fluid away from the affected portion of the patient.

14. A medical device in accordance with claim 1 comprising: stitches of varying lengths to provide different amounts of stretch to different portions of the medical device, said stitches including
    longer stitches for allowing the inner and outer layers to more comfortably conform to the body of the patient as the patient moves to help maintain constant compression and facilitate removal of excess fluid from the affected portion of the body of the patient; and
    shorter stitches for less stretch and a tighter fit of the medical device about the affected portion of the patient for helping prevent slippage of the medical device during wear of the medical device by the patient and for facilitating channeling and removal of excess fluid away from the affected portion of the patient.

15. A splinted assembly, comprising:
    a medical device in accordance with claim 1;
    a splint secured to the medical device;
    fabric overlay sewn or secured to the medical device over the splint, said fabric overlay cooperating with the medical device to provide a pocket for receiving the splint; and
    said pocket and said medical device cooperating for allowing lateral movement of the splint to accommodate movement of a patient's fingers, toes or other body portion extending from the splint and to reduce stiffness of the affected portion of the body and to enhance removal of excess fluid from the affected portion of the body of the patient.

16. A medical device for removal of excess fluids from body tissue, comprising:

a composite multilayered cylindrical-type assembly having flexible layers comprising an elastomeric layer comprising a central core; and a resilient layer secured to said elastomeric layer, said resilient layer selected from the group consisting of an array, series, set, matrix, pattern, and plurality of discrete spaced elastomeric components, channels between said spaced elastomeric components to enhance the flow of excess fluids from said body tissue, and each of said elastomeric components having a maximum span smaller than said elastomeric layer;

an outer cover enclosing said flexible layers, said outer cover comprising an outer protective sleeve with axially opposite end sections, said outer cover having a different composition and structure than said elastomeric layer and said resilient layer, comprising a tubular layer having a contacting portion comprising an inner layer for engaging or contacting the skin of a patient, said outer protective sleeve annularly surrounding said resilient layer and said elastomeric layer, said tubular layer being larger than the elastomeric components of said resilient layer, said axially opposite end sections being generally circular or disc-shaped, said strap being secured to axially opposite ends of said outer protective sleeve, and said strap extending outwardly from the outer cover, and radiating lines sewn into said device creating at least some of said channels.

17. A medical device in accordance with claim 16 wherein:

said outer cover comprises an elastic fabric layer comprising polyester-type fabric and/or a stretchable fabric comprising elastane fabric formed of polyurethane; and said elastomeric components are selected from the group consisting of foamed chips, foamed pieces, foamed parts, foamed sections, cut foam, and chopped foam; and said elastomeric components cooperating with each other to provide micro-zones of high and low pressure to facilitate movement of excess fluid away from the affected area or skin folds of the body of the patient.

18. A medical device for removal of excess fluids from body tissue, comprising:

a composite multilayered assembly for compressing body tissue of a patient in a controlled and graduated manner, said composite multilayered assembly having an outer layer;

an inner layer for engaging or contacting the skin about an affected portion of the body of a patient, said inner layer cooperating with said outer layer to enhance uniform distribution of compression about the affected portion of the patient; and flexible intermediate layers positioned between said outer layer and said inner layer, said flexible intermediate layers comprising an elastomeric layer having a different composition and structure than said inner and outer layers, said elastomeric layer being flexible to conform to the affected portion of the body of the patient; and a resilient layer secured to said elastomeric layer, said resilient layer having a different composition and structure than said inner and outer layers, said resilient layer selected from the group consisting of an array, series, set, matrix, pattern, and plurality of discrete spaced elastomeric components, channels between said spaced elastomeric components on a surface of said resilient layer to enhance flow of excess fluids from the body tissue of the patient, and each of said elastomeric components having a maximum span smaller than said elastomeric layer and being smaller than said outer layer and said inner layer, stitches of varying lengths to provide different amounts of stretch to different portions of the medical device, said stitches including longer stitches for allowing the inner and outer layers to more comfortably conform to the body of the patient as the patient moves to help maintain constant compression and facilitate removal of excess fluid from the affected portion of the body of the patient; and shorter stitches for less stretch and a tighter fit of the medical device about the affected portion of the patient for helping prevent slippage of the medical device during wear of the medical device by the patient and for facilitating channeling and removal of excess fluid away from the affected portion of the patient.

\* \* \* \* \*